United States Patent [19]

Brahler

[11] Patent Number: 5,496,218
[45] Date of Patent: Mar. 5, 1996

[54] COUPLING MEANS FOR THE DRIVE SHAFT OF PROPHY ANGLES

[75] Inventor: George R. Brahler, Lawrence, Kans.

[73] Assignee: Brahler Products, Inc., Lawrence, Kans.

[21] Appl. No.: 293,480

[22] Filed: Aug. 22, 1994

[51] Int. Cl.$^6$ ............................... A61C 1/12; F16D 1/104
[52] U.S. Cl. ................... 464/182; 464/177; 464/183; 433/125; 433/126; 403/341; 403/344; 403/375
[58] Field of Search ..................... 433/112, 125, 433/126, 127, 128, 129; 403/109, 309, 310, 311, 341, 344, 375; 464/172, 177, 183, 182

[56] References Cited

U.S. PATENT DOCUMENTS

| | | | |
|---|---|---|---|
| 308,639 | 12/1884 | Stevens | 403/344 |
| 348,131 | 8/1886 | Lea | 433/129 |
| 543,854 | 8/1895 | Davis | 433/126 |
| 5,209,658 | 5/1993 | Brahler | 433/115 |
| 5,219,285 | 6/1993 | Meller et al. | 433/126 |

Primary Examiner—Stephen Funk
Attorney, Agent, or Firm—Hovey, Williams, Timmons & Collins

[57] ABSTRACT

A coupling for the drive shaft of prophy angles includes an upper drive shaft with a finger-type clutch, and a lower drive shaft having a main drive shaft with a clutch receptacle, and having a drive shaft clamp. The main drive shaft has an expansion slot extending from side to side through the center of the main drive shaft and substantially along the length of the clutch receptacle. The drive shaft clamp also has an expansion slot extending from side to side through the center and substantially along the length of the drive shaft clamp. The drive shaft clamp fits over the clutch receptacle end of the main drive shaft with the expansion slots oriented perpendicular to each other allowing the finger-type clutch of the upper drive shaft assembly to be pressure fitted into the clutch receptacle. The upper drive shaft assembly is housed in a dental prophy angle, used to clean teeth, while the lower drive shaft is housed in a prophy handpiece having a controllable motor for rotating the lower drive shaft assembly. When the upper drive shaft assembly is coupled with the lower drive shaft assembly, the prophy angle is engaged with the prophy handpiece, and the controllable motor may rotate the coupled drive shaft assemblies.

7 Claims, 1 Drawing Sheet

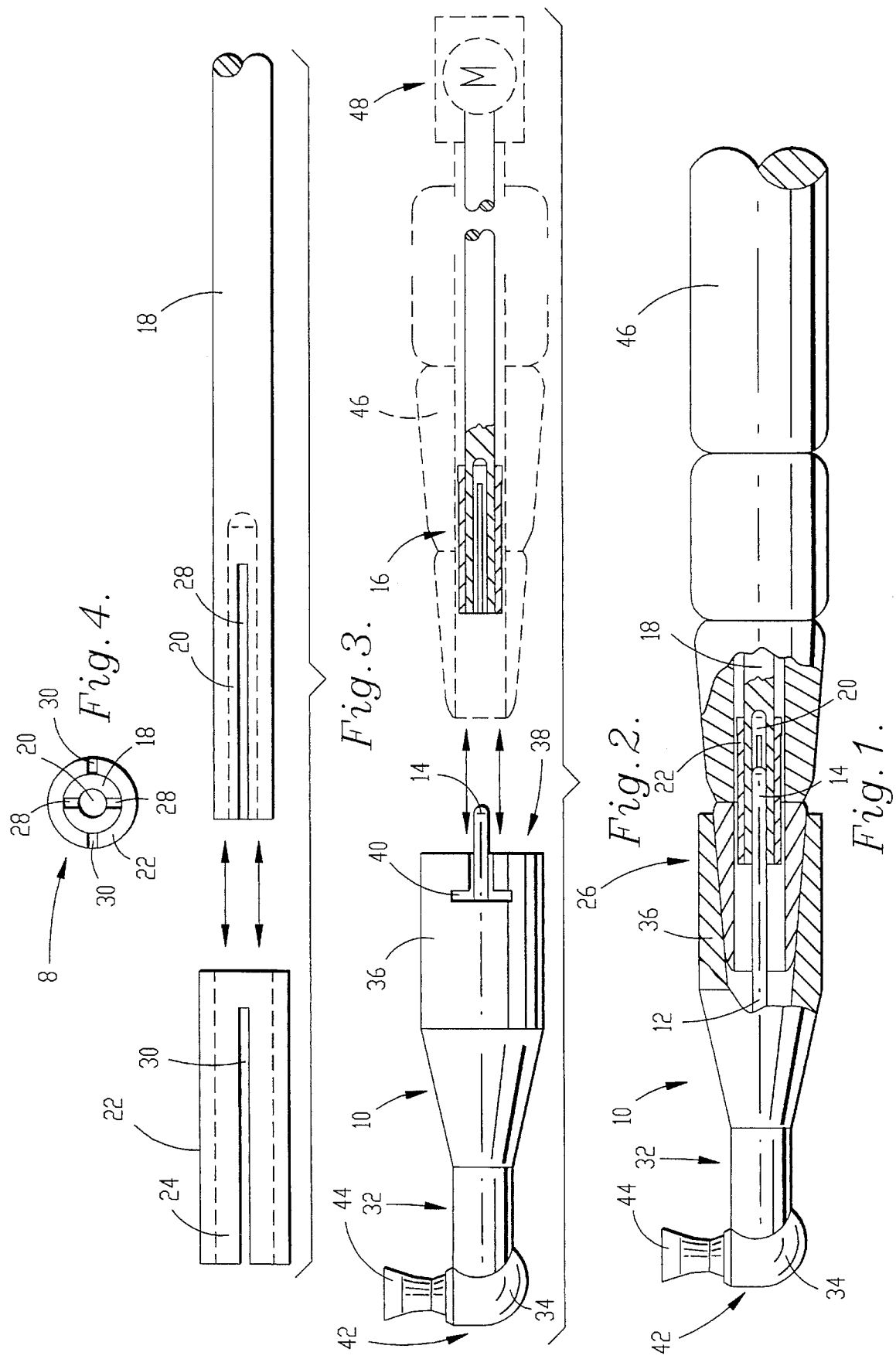

COUPLING MEANS FOR THE DRIVE SHAFT OF PROPHY ANGLES

BACKGROUND OF THE INVENTION

1. Field of the Invention

The present invention relates to the use of prophy angles in the field of dentistry for cleaning teeth, and, in particular, to an economically feasible disposable dental prophy angle having drive shaft coupling means including an upper drive shaft assembly with a finger-type clutch that engages a lower drive shaft assembly with a clutch receptacle located in a non-disposable prophy handpiece such that the coupling means minimizes wear exerted on the lower drive shaft assembly, and thus, maximizes the useful life of the prophy handpiece.

2. Discussion of the Prior Art

It is known to provide a dental prophy angle to polish and otherwise clean teeth. For example, it has long been the practice to provide prophy angles which engage a prophy handpiece, and are removable therefrom, to clean and polish the teeth of a person. Such removable prophy angles often house an upper drive shaft assembly which couples with the lower drive shaft assembly of the prophy handpiece when the prophy angle engages the prophy handpiece.

After being used to clean and polish the teeth of a person, the removable prophy angle is removed from the prophy handpiece and sanitized so as to avoid the spread of various contagious diseases and viruses. Because removable prophy angles are reusable, such prophy angles are often constructed of relatively durable, yet relatively expensive materials. However, removable prophy angles stand the risk of spreading contagious diseases and viruses if they are not properly sanitized between usage on different patients.

It is also known to provide a disposable dental prophy angle which is also removable from the prophy handpiece. Disposable prophy angles usually have the same design as the removable prophy angles; however, because such disposable prophy angles are used on only one patient and then discarded, disposable prophy angles are constructed of more economical materials. Disposable prophy angles offer a more effective method of preventing the spread of contagious diseases and viruses between successive patients, and also between the patient and the dentist or dental technician than do non-disposable prophy angles. Reference is made to my U.S. Pat. No. 3,740,853 issued Jun. 26, 1973; U.S. Pat. No. 3,869,877 issued Mar. 11, 1975; and U.S. Pat. No. 5,209,658 issued May 11, 1993.

In order for disposable prophy angles, to be economically feasible, they must be constructed of the aforementioned economical materials, examples of which include any of a number of synthetic resin materials suitable for such use. However, when constructed of such synthetic resin materials, the upper drive shaft assembly of a disposable prophy angle can cause damage to the lower drive shaft assembly of the non-disposable prophy handpiece when coupled thereto.

Therefore, a significant, and heretofore unsolved, problem exists to provide a coupling means for the drive shaft of a disposable prophy angle which minimizes the wear on, and increases the useful life of, the lower drive shaft assembly of a prophy handpiece while allowing the use of economical materials, such as any of a number of synthetic resin materials, in the construction of the upper drive shaft assembly of a disposable prophy angle.

SUMMARY OF THE INVENTION

It is an object of the present invention to provide a coupling means for the drive shaft of prophy angles which allows the use of economical materials in the construction of a disposable prophy angle, while minimizing the wear exerted on, and thereby maximizing the useful life of, the prophy handpiece.

In accordance with the present invention, a coupling means for the drive shaft of prophy angles is provided comprising an upper drive shaft assembly including a finger-type clutch with the shape of a pointing finger, a lower drive shaft assembly including a main drive shaft with a clutch receptacle, the clutch receptacle of the main drive shaft being engagable by the finger-type clutch of the upper drive shaft assembly, and a drive shaft clamp, the drive shaft clamp having an interior space engagable by the main drive shaft. In the coupled condition, the upper drive shaft assembly and the lower drive shaft assembly are coupled together forming a continuous drive shaft.

The main drive shaft has an expansion slot extending from side to side through the center of the main drive shaft substantially along the length of the clutch receptacle. The drive shaft clamp also has an expansion slot extending from side to side through the center of the drive shaft clamp, substantially along the length of the drive shaft clamp. The drive shaft clamp fits over the clutch receptacle end of the main drive shaft with the expansion slots being oriented perpendicular to each other.

The finger-type clutch is slightly larger than the clutch receptacle, so that the expansion slots allow the finger-type clutch to be pressure fitted into the clutch receptacle, retaining the finger-type clutch in the clutch receptacle, thereby presenting the coupled condition, while allowing forcible removal of the finger-type clutch from the clutch receptacle.

The upper drive shaft assembly is retained by a prophy angle including a housing having a head end and a shank end with a passageway extending through the housing from the head end to the shank end, an opening in the shank end, and a T-shaped expansion slot in the shank end. The upper drive shaft assembly is retained in the passageway and extends from the head end through the shank end with the finger-type clutch protruding out of the opening in the shank end.

The lower drive shaft assembly is retained in a prophy handpiece having a controllable motor for rotating the lower drive shaft assembly. When the upper drive shaft assembly and lower drive shaft assembly are in the coupled condition, the controllable motor rotates the upper drive shaft assembly as the lower drive shaft assembly is rotated.

The prophy handpiece is engagable by the prophy angle. The T-shaped expansion slot located in the shank end of the prophy angle allows the prophy angle to be pressure fitted to the prophy handpiece. When the prophy angle and prophy handpiece are so engaged, the upper drive shaft assembly and lower drive shaft assembly are also coupled. Therefore, engagement of the prophy angle with the prophy handpiece creates the coupled condition between the upper and lower drive shaft assemblies.

A gear box in the head end of the prophy angle is coupled with the upper drive shaft and shifts the rotational motion of the upper drive shaft ninety degrees. The gear box is connected to a workpiece, and affects rotational motion on the workpiece. Tooth paste, or another cleaning compound common to the field of dentistry, is applied to the workpiece which is then used by the dentist-operator or dental technician-operator to polish the teeth of the patient.

The upper drive shaft assembly and prophy angle may be constructed of any of a number of synthetic resin materials, thereby allowing economical production. The components of the lower drive shaft assembly may be constructed of any of a number of metallic materials which are suitable for such use.

A lower drive shaft assembly and upper drive shaft assembly thus described offer a coupling means for the drive shaft of prophy angles that is relatively inexpensive to produce, provides an economically feasible disposable prophy angle and upper drive shaft assembly, which promotes safe and sanitary use, while minimizing the wear exerted on the lower drive shaft assembly, thereby increasing the useful life of the prophy handpiece. Therefore, the coupling means for the drive shaft of prophy angles claimed below provides an economical means to achieve a relatively high degree of safety in the field of dentistry.

BRIEF DESCRIPTION OF THE DRAWINGS

A preferred embodiment of a coupling means for the drive shaft of prophy angles is described in detail below with reference to the attached figures, wherein:

FIG. 1 is a side elevational view of a dental prophy angle engaging a prophy handpiece, with portions being cut away to particularly disclose the coupling means for the drive shaft of prophy angles.

FIG. 2 is a side elevational view of a dental prophy angle with exposed finger-type clutch, and a shadow profile of a prophy handpiece, and a controllable motor.

FIG. 3 is a side elevational view of a lower drive shaft assembly, depicting the main drive shaft and drive shaft clamp.

FIG. 4 is an end elevational view of a lower drive shaft assembly.

DETAILED DESCRIPTION OF THE PREFERRED EMBODIMENT

A coupling means 8 for the drive shaft of prophy angles 10 constructed in accordance with a preferred embodiment of the present invention is illustrated in FIG. 1. The environment in which the coupling means 8 for the drive shaft of prophy angles 10 occurs generally takes the form of a dental device, such as a prophy angle mated to a prophy handpiece, which is used to clean and polish the teeth of patients in a dental lab or office. Generally, such a dental device is operated by a dentist or a dental technician.

In the illustrated example, the coupling means 8 for the drive shaft of prophy angle 10 comprises an upper drive shaft assembly 12 including a finger-type clutch 14, a lower drive shaft assembly 16 including a main drive shaft 18 with a clutch receptacle 20 that is engagable by the finger-type clutch 14, and a drive shaft clamp 22 with an interior space 24 that is engagable by the main drive shaft 18. The upper drive shaft assembly 12 and the lower drive shaft assembly 16 exist in the coupled condition 26 when the finger-type clutch 14 is inserted into the clutch receptacle 20.

Referring now to FIG. 3, the main drive shaft 18 with the clutch receptacle 20 has an expansion slot 28 extending from side to side through the center of the main drive shaft 18 substantially along the length of the clutch receptacle 20. The drive shaft clamp 22 also has an expansion slot 30 extending from side to side through the center and substantially along the length of the drive shaft clamp 22.

The main drive shaft 18 engages the interior space 24 of the drive shaft clamp 22 so that the drive shaft clamp 22 is pressure fitted over the clutch receptacle 20 end of the main drive shaft 18. As FIG. 4 discloses, the expansion slot 28 in the main drive shaft 18 is oriented perpendicular to the expansion slot 30 in the drive shaft clamp 22.

The exterior dimensions of the finger-type clutch 14 are slightly larger than the interior dimensions of the clutch receptacle 20. The expansion slots 28 and 30 allow the clutch receptacle 20 to expand slightly for receiving the finger-type clutch 14, thereby permitting the finger-type clutch 14 to be pressure fitted into the clutch receptacle 20. Pressure fitting the finger-type clutch 14 into the clutch receptacle 20 retains the finger-type clutch 14, thereby presenting the coupled condition 26, until forcible removal of the finger-type clutch 14 therefrom.

The upper drive shaft assembly 12 is retained by the prophy angle 10 including a housing 32 having a head end 34 and a shank end 36 with a passageway extending through the housing 32 from the head end 34 to the shank end 36, an opening 38 in the shank end 36, and a T-shaped expansion slot 40 also in the shank end 36, the upper drive shaft assembly 12 being retained in the passageway for rotational motion with the finger-type clutch 14 protruding out of the opening 38.

The prophy angle 10 further includes a gear box 42, retained in the head end 34, that is coupled with the upper drive shaft assembly 12 for shifting the rotational motion of the upper drive shaft assembly 12 ninety degrees. A workpiece 44 is connected to the gear box 42 so that the workpiece 44 is coupled with the upper drive shaft assembly 12 and rotates in a direction ninety degrees relative to the upper drive shaft assembly 12.

The lower drive shaft assembly 16 is retained in a prophy handpiece 46 having a controllable motor 48 for rotating the lower drive shaft assembly 16. The controllable motor 48 may be powered by any number of means, such as electrical or mechanical power.

The prophy handpiece 46 is engagable by the prophy angle 10, the T-shaped expansion slot 40 allowing the prophy angle 10 to be pressure fitted onto the prophy handpiece 46. As the prophy angle 10 engages the prophy handpiece 46, the finger-type clutch 14 engages the clutch receptacle 20. FIG. 1 illustrates the prophy angle 10 fully engaged with the prophy handpiece 46 and the upper 12 and lower 16 drive shaft assemblies in the coupled condition 26. The upper drive shaft assembly 12 may be rotated by the controllable motor 48 in the prophy handpiece 46 while in the coupled condition 26.

It will be observed that by the means discussed above, the coupling means 8 for the drive shaft of a prophy angle 10 may be used when coupling a prophy angle 10 with an upper drive shaft assembly 12 to a prophy handpiece 46 with a lower drive shaft assembly 16 for the purpose of cleaning and polishing teeth.

For example, the operator may apply tooth paste, or another cleaning compound common to the field of dentistry, to the workpiece 44 of the prophy angle 10. The controllable motor 48 may then be used to rotate the coupled drive shaft assemblies 12 and 16 at a selected rotational speed, such as between 0 and 4,000 revolutions per minute (RPM). The gear box 42 then shifts the rotational motion of the coupled drive shaft assemblies 12 and 16 ninety degrees and rotates the workpiece. The rapid rotational motion of the workpiece 44 combined with use of the dental compound effectively cleans and polishes teeth.

The gear box 42 may be a direct gear box, which rotates the workpiece once for every revolution of the drive shaft assemblies 12 and 16, a reduction gear box, which rotates the workpiece less than once for every revolution of the drive shaft assemblies 12 and 16, or an addition gear box, which rotates the workpiece 44 more than once for each revolution of the drive shaft assemblies 12 and 16.

Once the teeth of a patient have been cleaned and polished, the prophy angle 10 is removed from the prophy handpiece 46 by uncoupling the upper drive shaft assembly 12 from the lower drive shaft assembly 16, and properly disposed of in an appropriate waste receptacle.

It will also be observed by the means discussed above, that the coupling means 8 for the drive shaft of a prophy angle 10 permits full use of a prophy angle 10 for cleaning and polishing teeth, while allowing relatively quick and convenient separation of the prophy angle 10 from the prophy handpiece 46 for the purpose of changing the prophy angle 10 for sanitary reasons. The finger-type clutch 14 of the upper drive shaft assembly 12 easily couples with the clutch receptacle 20 of the lower drive shaft assembly 16 when the prophy angle 10 engages the prophy handpiece 46.

When the lower drive shaft assembly 16 is constructed of any of a number of metallic materials, and the upper drive shaft assembly 12 is constructed of any of a number of synthetic resin materials, a minimum of damage and wear is caused to the lower drive shaft assembly 16. Thus, a prophy handpiece 46 with such a lower drive shaft assembly 16 is durable and may be used for relatively long periods of time.

Additionally, the coupling means 8 for the drive shaft of prophy angles 10 allows a disposable prophy angle 10 to be constructed of economical materials without causing the aforementioned damage to the lower drive shaft assembly 16, thereby promoting safe and sanitary usage of prophy angles 10. These factors are important for dental offices which have many patients each day who are in need of teeth cleaning.

Although a coupling means 8 for the drive shaft of prophy angles 10 has been described with reference to the illustrated figures, it is noted that variations and changes may be made and equivalents employed herein without departing from the scope of the invention as recited in the claims.

I claim:

1. A coupling means for a drive shaft of prophy angles comprising:

an upper drive shaft assembly including a finger-type clutch, said finger-type clutch having the shape of a pointing finger;

a lower drive shaft assembly including a main drive shaft with a clutch receptacle located at one end of said drive shaft, and a drive shaft clamp, said clutch receptacle engagable by said finger-type clutch, said drive shaft clamp having an interior space engagable by said main drive shaft;

said main drive shaft with said clutch receptacle having an expansion slot extending from side to side through the center of the main drive shaft substantially along the length of the clutch receptacle;

said drive shaft clamp having an expansion slot extending from side to side through the center of the main drive shaft clamp, and substantially along the length of the drive shaft clamp;

said drive shaft clamp fitting over said clutch receptacle end of main drive shaft, said expansion slots being oriented perpendicular to each other; and a coupled condition of said upper drive shaft assembly and said lower drive shaft assembly being created when said finger-type clutch engages said clutch receptacle by inserting said finger-type clutch into said clutch receptacle.

2. A coupling means for a drive shaft of prophy angles as set forth in claim 1, said upper drive assembly being retained by a dental prophy angle which includes a housing having a head end and a shank end with a passageway extending through said housing between said ends, an opening in said shank end, and a T-shaped expansion slot in said shank end, said upper drive shaft assembly being retained by said housing, and extending from said head end to said shank end through said passageway for relative rotational movement, said finger-type clutch of said upper drive shaft assembly protruding from said shank end of said housing.

3. A coupling means for a drive shaft of prophy angles as set forth in claim 2, said lower drive shaft being retained by a prophy handpiece engagable by said prophy angle, said prophy handpiece having a controllable motor for rotating said lower drive shaft assembly.

4. A coupling means for a drive shaft of prophy angles as set forth in claim 3, said coupled condition of said upper drive shaft assembly and said lower drive shaft assembly occurring when said prophy angle engages said prophy handpiece, said upper drive shaft assembly being rotatable by said controllable motor when said upper drive shaft assembly and said lower drive shaft assembly are in said coupled condition.

5. A coupling means for a drive shaft of prophy angles as set forth in claim 4, wherein said finger-type clutch defines exterior dimensions, and said clutch receptacle defines interior dimensions, said finger-type clutch exterior dimensions being slightly larger than said clutch receptacle interior dimensions, said expansion slots in said main drive shaft and said drive shaft clamp allowing said clutch receptacle to expand slightly as said clutch is inserted into said clutch receptacle.

6. A coupling for a drive shaft of prophy angles as set forth in claim 5, said upper drive shaft assembly with said finger-type clutch being constructed of a synthetic resin material.

7. A coupling for a drive shaft of prophy angles as set forth in claim 6, said lower drive shaft assembly being constructed of a metallic material.

\* \* \* \* \*